United States Patent
Chen et al.

(10) Patent No.: US 11,179,032 B2
(45) Date of Patent: Nov. 23, 2021

(54) CALIBRATION METHOD AND DEVICE OF SYSTEM FOR MEASURING CORNEAL PARAMETERS

(71) Applicant: WENZHOU MEDICAL UNIVERSITY, Wenzhou (CN)

(72) Inventors: Hao Chen, Wenzhou (CN); Jinhai Huang, Wenzhou (CN); Hang Yu, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 231 days.

(21) Appl. No.: 16/618,086

(22) PCT Filed: Jan. 25, 2019

(86) PCT No.: PCT/CN2019/073063
§ 371 (c)(1),
(2) Date: Nov. 27, 2019

(87) PCT Pub. No.: WO2019/154101
PCT Pub. Date: Aug. 15, 2019

(65) Prior Publication Data
US 2020/0100669 A1    Apr. 2, 2020

(30) Foreign Application Priority Data
Feb. 11, 2018  (CN) .......................... 201810143022.1

(51) Int. Cl.
*A61B 3/10*     (2006.01)
*A61B 3/103*    (2006.01)
(Continued)

(52) U.S. Cl.
CPC ............ *A61B 3/1005* (2013.01); *A61B 3/103* (2013.01); *A61B 3/107* (2013.01); *A61B 3/135* (2013.01); *A61B 3/14* (2013.01)

(58) Field of Classification Search
CPC ....... A61B 3/1005; A61B 3/103; A61B 3/107; A61B 3/135; A61B 3/14; A61B 3/0025
(Continued)

(56) References Cited

U.S. PATENT DOCUMENTS

| | | | |
|---|---|---|---|
| 2007/0253688 A1 | 11/2007 | Koennecke | |
| 2008/0144035 A1* | 6/2008 | Allred | A61B 3/0025 356/446 |
| 2009/0096987 A1 | 4/2009 | Lai et al. | |

FOREIGN PATENT DOCUMENTS

| | | | |
|---|---|---|---|
| CN | 1873654 A | * | 12/2006 |
| CN | 1901833 A | | 1/2007 |

(Continued)

OTHER PUBLICATIONS

Chinese Office Action for Application No. 20180143022.1, dated Aug. 17, 2020, 12 pages.

*Primary Examiner* — Mohammed A Hasan
(74) *Attorney, Agent, or Firm* — Womble Bond Dickinson (US) LLP

(57) ABSTRACT

The invention provides a calibration method and a calibration device of a system for measuring corneal parameters, and particularly the invention provides a system calibration method and device for geometric distortion, caused by camera shooting angle when measuring cornea-related parameters, of a digital slit lamp and a system of similar principles based on machine vision. The method of the invention comprises the steps of: placing a calibration block on a calibration stand, using a slit lamp to shine light perpendicularly to the calibration block, and then photographing in a manner that four vertexes of a cross section are all within a visual range of a digital camera, so as to obtain the four corners and thus corresponding four edges of the cross section; restoring the position of a real image in the image using a ray tracing method; and then performing (Continued)

geometric distortion correction according to real-image coordinates of the four corners in the image and corresponding real-space lengths thereof, thus geometric distortion caused by the camera shooting angle can be eliminated, and the real dimension represented by each pixel can be obtained.

10 Claims, 4 Drawing Sheets

(51) Int. Cl.
*A61B 3/107* (2006.01)
*A61B 3/135* (2006.01)
*A61B 3/14* (2006.01)

(58) Field of Classification Search
USPC .......................................................... 351/206
See application file for complete search history.

(56) References Cited

FOREIGN PATENT DOCUMENTS

| CN | 104720740 A | | 6/2015 | |
|---|---|---|---|---|
| CN | 104883957 A | * | 9/2015 | ........... A61B 3/1015 |
| CN | 105590328 B | * | 4/2018 | |
| CN | 108420401 A | | 8/2018 | |

* cited by examiner

CALIBRATION METHOD AND DEVICE OF SYSTEM FOR MEASURING CORNEAL PARAMETERS

CROSS REFERENCE TO RELATED APPLICATIONS

This is a U.S. National Stage Application, filed under 35 U.S.C. 371, of International Patent Application No. PCT/CN2019/073063, filed on Jan. 25, 2019, which claims priority to Chinese Patent Application No. 201810143022.1, filed on Feb. 11, 2018, the disclosures of which are incorporated herein by reference in their entirety.

TECHNICAL FIELD

The invention relates to the field of optical detection, in particular to a calibration method and device of a system for measuring corneal parameters.

BACKGROUND ART

The cornea is the transparent front part of the eye that covers the iris, pupil and anterior chamber and provides 70% refractive power of the eye. Minor changes in the cornea can cause great changes in the refractive state. Therefore, people have been committed to studying the geometry and optical characteristics of the cornea. Accurate measurements of corneal curvature and central corneal thickness (CCT) provide important basis for early diagnosis of corneal diseases, preoperative screening and postoperative follow-up of corneal refractive surgery and intraocular lens power calculation, and are also of great significance in correcting intraocular pressure, screening for glaucoma, etc.

The full name of a slit lamp is "slit lamp microscope", which is a commonly used optical instrument in ophthalmology. The eyelids, conjunctiva, sclera, cornea, anterior chamber, iris, pupil, lens and the anterior ⅓ of vitreous body can be clearly seen through the slit lamp microscope, thus the location, property, size and depth of the lesion can be determined. By making appropriate improvements to a slit lamp system, such as adding digital modules and other components, or by developing similar equipment according to measurement principle of the slit lamp, relevant parameters such as corneal thickness and curvature can be measured. In order to ensure the accuracy of the cornea-related parameters, accurate calibration of the system is essential.

SUMMARY OF THE INVENTION

The invention aims to provide a calibration method of a system for measuring corneal parameters.

A first aspect of the invention provides a calibration method of a system for measuring corneal parameters, the method comprising the steps of:

1) providing a calibration block which is a transparent cuboid;

2) shining a slit lamp on the calibration block in an optical path perpendicular to the calibration block to form an optical cross section, and using a camera to photograph at an angle deviating from the optical path of the slit lamp by a to capture an image of the optical cross section, ensuring that an upper surface, a lower surface, a front surface and a rear surface of the transparent calibration block are all within an angle of view of the camera; and 3) correcting the image using a geometric distortion correction method, and according to real three-dimensional data of the calibration block, calculating an actual distance represented by each pixel in the image in a focused and clear state, for conversion of a corneal thickness in the image to a real corneal thickness.

Further, the refractive index of the calibration block is equal to the refractive index of a cornea.

Further, the refractive index of the calibration block is known in the step 1), such as being 1.376.

Further, in the step 2), the camera photographs the calibration block at a fixed angle which is the same as the shooting angle when measuring cornea-related parameters.

Further, the four corners of the image of the cross section are obtained by using a corner detection method in image processing and then corresponding four edges are obtained in the step 3).

Further, in the step 3), since the image formed by the rear surface of the calibration block is a virtual image, the position of a real image of the rear surface of the calibration block in the image is restored first according to a ray tracing method, and then geometric distortion correction is performed according to real-image coordinates of the four corners in the image and corresponding real-space lengths.

A second aspect of the invention provides a calibration device of a system for measuring corneal parameters, the device comprising: a calibration block, a slit lamp system, a camera and a data processing unit;

wherein the calibration block is a transparent cuboid; the slit lamp system is configured for emitting light in an optical path perpendicular to the calibration block to form an optical cross section; the camera is configured for photographing at an angle deviating from the optical path of the slit lamp by a to capture an image of the optical cross section and transmitting the captured image to the data processing unit; and the data processing unit calibrates the image based on the captured image of the cross section using a geometric distortion correction method, and according to real three-dimensional data of the calibration block, calculates an actual distance represented by each pixel in the image in a focused and clear state, for conversion of a corneal thickness in the image to a real corneal thickness.

Further, the refractive index of the calibration block is equal to the refractive index of a cornea.

Further, the refractive index of the calibration block is known, such as being 1.376.

Further, four corners of the cross section of the calibration block are within a range of the slit lamp.

Further, the device is configured to perform the method according to the first aspect of the invention.

Further, the device further comprises a calibration stand configured for fixing the calibration block.

DETAILED DESCRIPTION OF EMBODIMENTS

The invention relates to a system calibration method for geometric distortion, caused by camera shooting angle when measuring cornea-related parameters, of a digital slit lamp and a system of similar principles based on machine vision.

The method of the invention comprises the following steps: A transparent cuboid with known three dimensions is taken as a calibration block and placed on a calibration stand, and the included angle between the camera and the illumination direction of the slit lamp is a fixed angle when measuring cornea-related parameters. A digital slit lamp is used to shine light perpendicularly to a cross section of the calibration block, then photographing is performed in a manner that four vertexes of the cross section are all within a visual range of the digital camera, the four corners of the cross section are obtained by using a corner detection method in image processing, and thereby corresponding four edges are obtained. Since the refractive index of the transparent calibration block is different from that of air, the image formed by a rear surface of the calibration block is a virtual image, and the position of its real image in the image is restored by a ray tracing method. Then, according to real-image coordinates of the four corners in the image and corresponding real-space lengths thereof, geometric distortion correction is performed, thus geometric distortion caused by the camera shooting angle can be eliminated, and the real dimension represented by each pixel can be obtained.

Figure 1:
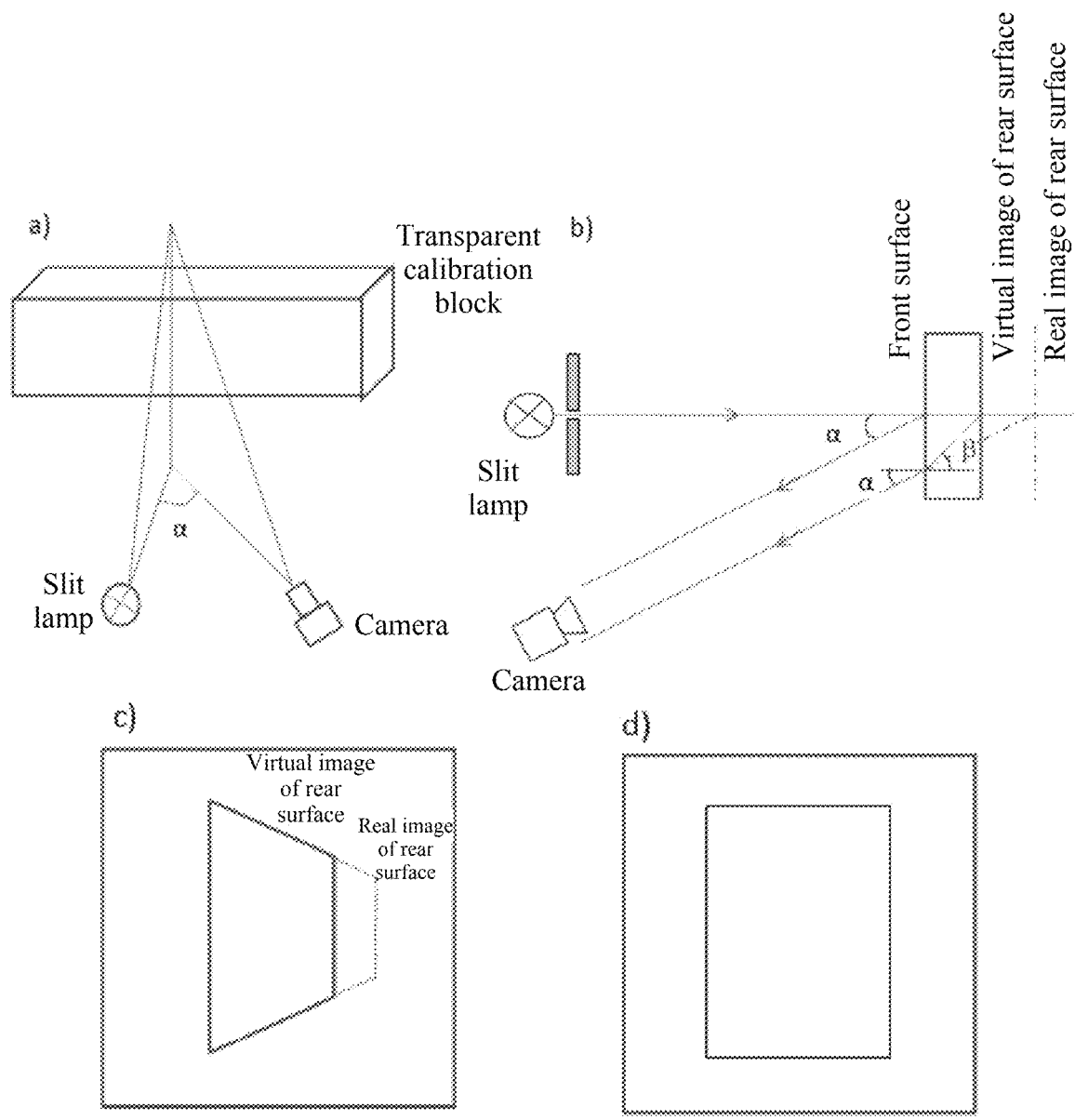
FIG. 1 shows the principle of calibration according to the invention, wherein a) is a schematic diagram (front view) of calibration according to the invention; b) is a schematic diagram (top view) of calibration according to the invention; c) is a calibration block image taken by a camera; and d) is a calibration block image after geometric distortion correction.

As shown in FIG. 1, according to the calibration method of the invention, a transparent cuboid with known three dimensions is used as a calibration block. The illumination light path of the slit lamp is directed towards the calibration block to be perpendicular to and illuminate a cross section of the calibration block. The camera shooting direction is offset from the illumination light path by a fixed angle α (the included angle is a conventional fixed angle used for photographing the cornea when measuring corneal parameters, for example, an angle fixing device can be placed at that angle), as shown in a) of FIG. 1, which angle is the same as the angle used when measuring cornea-related parameters with the slit lamp.

Then the position of the calibration block is adjusted to the clearest imaging point, i.e. the focal point, to ensure that the upper surface, lower surface, front surface and rear surface of the transparent calibration block are all within a camera viewing angle, as shown in b) of FIG. 1.

Since the refractive index of the material of the transparent calibration block is not equal to 1, the rear surface is imaged as a virtual image, and the rear surface needs to be adjusted according to the ray tracing method. The adjusted rear surface is indicated by a dashed line, as shown by the dashed line in b) of FIG. 1 and c) of FIG. 1.

Since the camera shooting angle is not parallel to the plane being photographed, the image will have geometric distortion, i.e. the rectangular object is shown as a trapezoid in the image, as shown in c) of FIG. 1. The image is corrected by the geometric distortion correction method, and the corrected image is shown in d) of FIG. 1.

Since the real three-dimensional data of the calibration block are known, an actual distance represented by each pixel in the image in a focused and clear state can be calculated and used for conversion of a corneal thickness in the image to a real corneal thickness. The length, width and height of the calibration block are selected according to the field of vision of the digital slit lamp, so long as the four corners of the cross section of the calibration block are within the range of the slit lamp.

Figure 2:
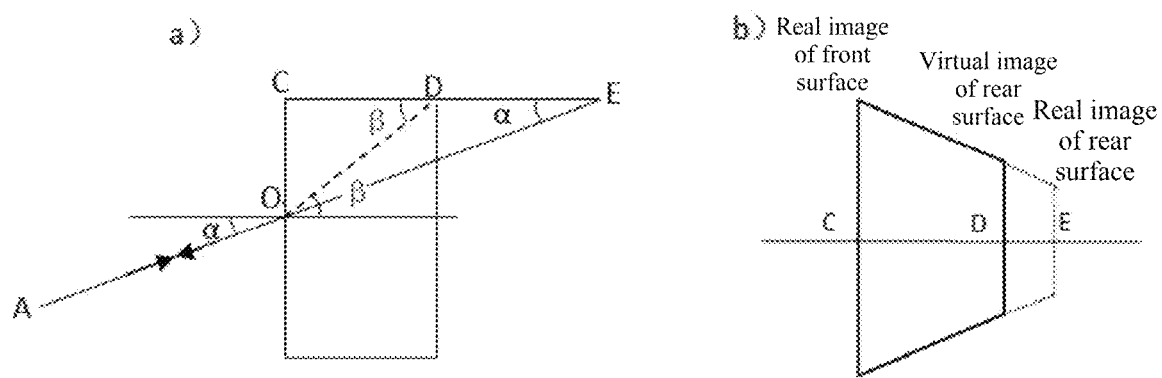
FIG. 2 shows a ray tracing method, where a) shows the principle of the ray tracing method; and b) shows the position in the image corresponding to the ray tracing method.

As shown in FIG. 2, the method for obtaining the real-image position of the rear surface of the cross section of the calibration block is as follows: The refractive index of the calibration block is 1.376, so the light ray AO will be refracted when entering and leaving the calibration block, where OD is the refracted light path, and OE is the original direction of the light path if no refraction occurs, as shown in the figure. The refractive index n of the calibration block is known, and the angle β can be obtained according to the refractive index equation and the light refraction equation $n=1.376=\sin \beta / \sin \alpha$. Then, according to the trigonometric formula 1, a image length $l_{DE}$ by which the rear surface D of the cross section of the calibration block should move backward can be obtained to further obtain the real-image position E, and then according to the schematic diagram in b) of FIG. 2, the position of the real image of the rear surface in the image can be obtained:

$$l_{CD} \times \tan \beta = (l_{CD} + l_{DE}) \times \tan \alpha \qquad \text{Formula 1.}$$

Figure 4:
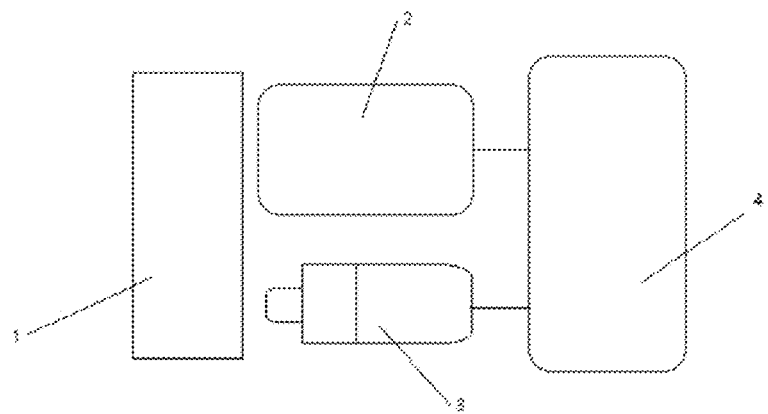
FIG. 4 is a structural schematic diagram of a calibration device of a system for measuring corneal parameters according to a preferred embodiment of the invention.

As shown in FIG. 4, a calibration device of a system for measuring corneal parameters provided by the invention comprises: a calibration block 1, a slit lamp system 2, a camera 3 and a data processing unit 4;

wherein the calibration block 1 is a transparent cuboid; the slit lamp system 2 is configured for emitting light in an optical path perpendicular to the calibration block 1 to form an optical cross section; the camera 3 is configured for photographing at an angle deviating from the optical path of the slit lamp by α to capture an image of the optical cross section and transmitting the captured image to the data processing unit 4; and the data processing unit 4 calibrates the image based on the captured image of the cross section using a geometric distortion correction method, and according to real three-dimensional data of the calibration block, calculates an actual distance represented by each pixel in the image in a focused and clear state, for conversion of a corneal thickness in the image to a real corneal thickness.

Figure 3:
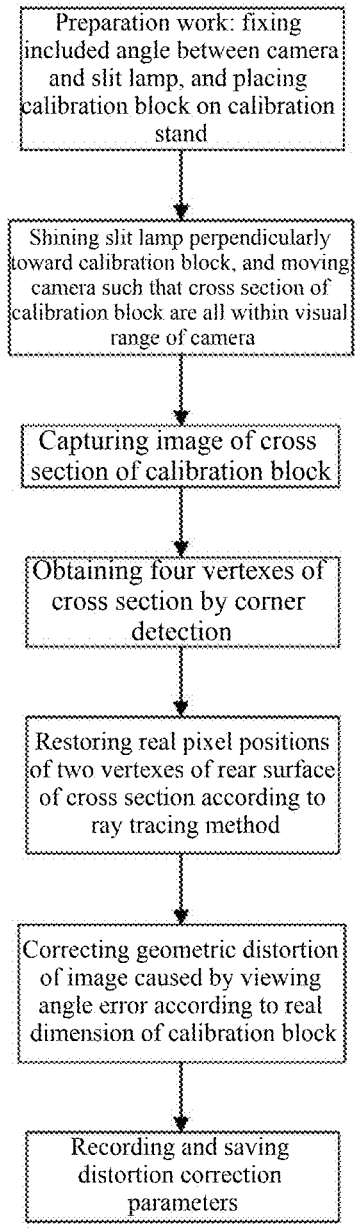
FIG. 3 is a flowchart of a calibration method according to a preferred embodiment of the invention.

The detection process is carried out with reference to the flowchart of FIG. 3, and thus the calibration of the system for measuring corneal parameters can be realized.

All documents mentioned in this application are hereby incorporated by reference as if each document were individually incorporated by reference. In addition, it should be understood that after reading the above teachings of the invention, those skilled in the art can make various changes or modifications to the invention, and these equivalent forms also fall within the scope defined by the appended claims of this application.

The invention claimed is:

1. A calibration method of a system for measuring corneal parameters, the method comprising the steps of:
   1) providing a calibration block which is a transparent cuboid;
   2) shining a slit lamp on the calibration block in an optical path perpendicular to the calibration block to form an optical cross section, and using a camera to photograph at an angle deviating from the optical path of the slit lamp by a to capture an image of the optical cross section, ensuring that an upper surface, a lower surface, a front surface and a rear surface of the transparent calibration block are all within an angle of view of the camera; and 3) correcting the image using a geometric distortion correction method, and according to real three-dimensional data of the calibration block, calculating an actual distance represented by each pixel in the image in a focused and clear state, for conversion of a corneal thickness in the image to a real corneal thickness.

2. The method of claim 1, wherein the refractive index of the calibration block is equal to or not equal to the refractive index of a cornea.

3. The method of claim 2, wherein the refractive index of the calibration block is known in the step 1).

4. The method of claim 1, wherein four corners of the cross section of the calibration block are within a range of the slit lamp in the step 1).

5. The method of claim 1, wherein the four corners of the image of the cross section are obtained by using a corner detection method in image processing and then corresponding four edges are obtained in the step 3).

6. A calibration device of a system for measuring corneal parameters, the device comprising: a calibration block, a slit lamp system, a camera and a data processing unit;

wherein the calibration block is a transparent cuboid; the slit lamp system is configured for emitting light in an optical path perpendicular to the calibration block to form an optical cross section; the camera is configured for photographing at an angle deviating from the optical path of the slit lamp by a to capture an image of the optical cross section, which angle is the same as a shooting angle for measuring cornea-related parameters, and transmitting the captured image to the data processing unit; and the data processing unit calibrates the image based on the captured image of the cross section using a geometric distortion correction method, and according to real three-dimensional data of the calibration block, calculates an actual distance represented by each pixel in the image in a focused and clear state, for conversion of a corneal thickness in the image to a real corneal thickness.

7. The device of claim 6, wherein the refractive index of the calibration block is equal to or not equal to the refractive index of a cornea.

8. The device of claim 6, wherein the refractive index of the calibration block is known.

9. The device of claim 6, wherein four corners of the cross section of the calibration block are within a range of the slit lamp.

10. The device of claim 6, wherein the device is configured to perform the method of claim 1.

* * * * *